(12) United States Patent
Stahmann et al.

(10) Patent No.: US 11,666,749 B2
(45) Date of Patent: Jun. 6, 2023

(54) IMPLANTABLE DEVICES AND METHODS FOR CONTROL OF BACTERIAL INFECTIONS

(71) Applicant: Cardiac Pacemakers, Inc., St. Paul, MN (US)

(72) Inventors: Jeffrey E. Stahmann, Ramsey, MN (US); Keith R. Maile, New Brighton, MN (US); Danielle Frankson, Dayton, MN (US); Craig M. Stolen, New Brighton, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 17/076,313

(22) Filed: Oct. 21, 2020

(65) Prior Publication Data

US 2021/0121683 A1 Apr. 29, 2021

Related U.S. Application Data

(60) Provisional application No. 62/924,983, filed on Oct. 23, 2019.

(51) Int. Cl.
| | |
|---|---|
| *A61N 1/05* | (2006.01) |
| *A61N 1/39* | (2006.01) |
| *A61N 1/378* | (2006.01) |
| *A61N 1/36* | (2006.01) |
| *A61L 2/03* | (2006.01) |

(Continued)

(52) U.S. Cl.
CPC .............. *A61N 1/0504* (2013.01); *A61L 2/03* (2013.01); *A61N 1/36185* (2013.01); *A61N 1/372* (2013.01); *A61N 1/3787* (2013.01); *A61N 1/3918* (2013.01); *A61N 1/39622* (2017.08); *A61B 18/18* (2013.01)

(58) Field of Classification Search
CPC .............................. A61N 1/372; A61N 1/0504
USPC ........................................................ 128/897
See application file for complete search history.

(56) References Cited

U.S. PATENT DOCUMENTS

| | | |
|---|---|---|
| 9,039,764 B2 | 5/2015 | Gilbert |
| 9,320,832 B2 | 4/2016 | Joseph et al. |
| 9,616,142 B2 | 4/2017 | Ehrensberger et al. |

(Continued)

FOREIGN PATENT DOCUMENTS

| | | | | |
|---|---|---|---|---|
| WO | WO-2012177807 A1 | * | 12/2012 | ............. A61L 29/02 |
| WO | WO-2017157894 A1 | * | 9/2017 | ............ A61B 5/1451 |

*Primary Examiner* — Nicole F Lavert
(74) *Attorney, Agent, or Firm* — Nelson Mullins Riley & Scarborough LLP

(57) ABSTRACT

An implantable antibacterial barrier device for an elongated medical device, the elongated medical device configured to extend from a first site, through a second site, to a third site. The implantable antibacterial barrier device includes a housing configured to be disposed at the first site, a working electrode configured to be disposed at the second site, and a reference electrode configured to be disposed at the first site. The housing includes barrier circuitry. The working electrode electrically is coupled to the barrier circuitry. The reference electrode is electrically coupled to the barrier circuitry. The barrier circuitry is configured to selectively maintain the working electrode at a negative electrical potential relative to the reference electrode to form an antibacterial barrier.

20 Claims, 6 Drawing Sheets

(51) Int. Cl.
*A61N 1/372* (2006.01)
*A61B 18/18* (2006.01)

(56) References Cited

U.S. PATENT DOCUMENTS

| | | | |
|---|---|---|---|
| 2006/0004431 A1 | 1/2006 | Fuller et al. | |
| 2015/0088155 A1* | 3/2015 | Stahmann | A61N 1/0587 |
| | | | 606/129 |
| 2017/0303840 A1* | 10/2017 | Stadler | A61N 7/02 |
| 2019/0192864 A1* | 6/2019 | Koop | A61N 1/057 |

* cited by examiner

IMPLANTABLE DEVICES AND METHODS FOR CONTROL OF BACTERIAL INFECTIONS

CROSS REFERENCE TO RELATED APPLICATION

This application claims priority to Provisional Application No. 62/924,983, filed Oct. 23, 2019, which is herein incorporated by reference in its entirety.

TECHNICAL FIELD

The present disclosure relates preventing infections associated with implantable medical devices. More specifically, the invention relates to devices and methods for preventing infections associated with medical devices implanted in a patient.

BACKGROUND

Medical devices may be implanted in a patient to support sensing intrinsic physiological electrical activity, delivering a therapeutic stimulus to patient tissue, or providing other therapy to specific treatment sites. For example, a pulse generator may be implanted in a subcutaneous pocket in a patient's chest, with one or more electrical leads extending from the pulse generator in the subcutaneous pocket and into the vasculature to treatment sites within the patient. In another example, a drug delivery pump may be implanted in a subcutaneous pocket, with a catheter extending from the drug delivery pump and into the vasculature to the treatment site requiring the drug.

Implanting a medical device in a subcutaneous pocket within a patient inherently exposes the patient to a risk of a nosocomial (e.g., hospital-acquired) bacterial infection. A bacterial infection beginning within the subcutaneous pocket can spread along the lead or catheter and travel into the vasculature and to a treatment site, such as the heart. Bacterial infections in the vasculature and in the heart are more serious and more difficult to treat than bacterial infections in the subcutaneous pocket.

SUMMARY

Example 1 is an implantable antibacterial barrier device for an elongated medical device, the elongated medical device configured to extend from a first site, through a second site, to a third site. The implantable antibacterial barrier device includes a housing configured to be disposed at the first site, a working electrode configured to be disposed at the second site, and a reference electrode configured to be disposed at the first site. The housing includes barrier circuitry. The working electrode electrically is coupled to the barrier circuitry. The reference electrode is electrically coupled to the barrier circuitry. The barrier circuitry is configured to selectively maintain the working electrode at a negative electrical potential relative to the reference electrode to form an antibacterial barrier.

Example 2 is the implantable antibacterial barrier device of Example 1, wherein the first site is a subcutaneous pocket.

Example 3 is the implantable antibacterial barrier device of Example 1 or Example 2, wherein the second site is adjacent to a vascular entry site and the elongated medical device extends through the vascular entry site and through a portion of a vascular system to the third site.

Example 4 is the implantable antibacterial barrier device of any of Examples 1-3, wherein the third site is at least one selected from the group of a treatment site and a measurement site.

Example 5 is the implantable antibacterial barrier device of any of Examples 1-4, wherein the reference electrode is configured to be spaced apart from the working electrode by at least 1 cm.

Example 6 is the implantable antibacterial barrier device of any of Examples 1-5, wherein the working electrode is further configured to be disposed at least partially around the elongated medical device.

Example 7 is the implantable antibacterial barrier device of any of Examples 1-6, wherein the reference electrode includes at least a portion of an exterior surface of the housing.

Example 8 is the implantable antibacterial barrier device of any of Examples 1-6, wherein the reference electrode includes a patch electrode.

Example 9 is the implantable antibacterial barrier device of any of Examples 1-6, wherein the reference electrode is further configured to be disposed at least partially around the elongated medical device.

Example 10 is the implantable antibacterial barrier device of Example 9, further including an electrode spacer, the working electrode and the reference electrode physically coupled to the electrode spacer.

Example 11 is the implantable antibacterial barrier device of any of Examples 1-10, wherein the housing further includes an energy storage device electrically coupled to the barrier circuitry.

Example 12 is the implantable antibacterial barrier device of any of Examples 1-11, wherein the housing further includes a wireless power receiver electrically coupled to the barrier circuitry.

Example 13 is an implantable medical device including an elongated medical device and the implantable antibacterial barrier device of any of Examples 1-12. The elongated medical device configured to extend from the first site, through the second site, to the third site.

Example 14 is the implantable medical device of Example 13, wherein the elongated medical device is an electrical lead having a proximal end configured to be coupled to the housing and a distal end configured be disposed adjacent to the third site. The implantable medical device further includes stimulation circuitry contained within the housing for providing electro stimulation therapy at the third site, and a treatment electrode configured to be electrically coupled to the stimulation circuitry. The treatment electrode is disposed at the distal end.

Example 15 is the implantable medical device of Example 13, wherein the working electrode is integral with the electrical lead.

Example 16 is the implantable medical device of Example 13, wherein the elongated medical device is a catheter having a proximal end configured to be coupled to the housing and a distal end configured to be disposed adjacent to the third site, the implantable medical device further including a pump contained within the housing for providing chemical therapy to the third site.

Example 17 is a method for providing an antibacterial barrier between a subcutaneous pocket and vascular entry site. The method includes disposing a reference electrode in a subcutaneous pocket, disposing a working electrode adjacent to the vascular entry site, and generating an electrical potential at the working electrode that is negative relative to the reference electrode.

Example 18 is an implantable antibacterial barrier device for an elongated medical device, the elongated medical device configured to extend from a first site, through a second site, to a third site. The implantable antibacterial barrier device includes a housing configured to be disposed at the first site, a working electrode configured to be disposed at the second site, and a reference electrode configured to be disposed at the first site and spaced apart from the working electrode. The housing includes barrier circuitry. The working electrode electrically is coupled to the barrier circuitry. The reference electrode is electrically coupled to the barrier circuitry. The barrier circuitry is configured to selectively maintain the working electrode at a negative electrical potential relative to the reference electrode to form an antibacterial barrier.

Example 19 is the implantable antibacterial barrier device of Example 18, wherein the first sited is a subcutaneous pocket.

Example 20 is the implantable antibacterial barrier device of Example 18 or Example 19, wherein the second site is adjacent to a vascular entry site and the elongated medical device extends through the vascular entry site and through a portion of a vascular system to the third site.

Example 21 is the implantable antibacterial barrier device of any of Examples 18-20, wherein the third site is at least one selected from the group of a treatment site and a measurement site.

Example 22 is the implantable antibacterial barrier device of any of Examples 18-22, wherein the reference electrode is configured to be spaced apart from the working electrode by at least 1 cm.

Example 23 is the implantable antibacterial barrier device of any of Examples 18-22, wherein the working electrode is further configured to be disposed at least partially around the elongated medical device.

Example 24 is the implantable antibacterial barrier device of any of Examples 18-23, wherein the reference electrode includes at least a portion of an exterior surface of the housing.

Example 25 is the implantable antibacterial barrier device of any of Examples 18-23, wherein the reference electrode includes a patch electrode.

Example 26 is the implantable antibacterial barrier device of any of Examples 18-23, wherein the reference electrode is further configured to be disposed at least partially around the elongated medical device.

Example 27 is the implantable antibacterial barrier device of any of Examples 18-26, wherein the housing further includes an energy storage device electrically coupled to the barrier circuitry.

Example 28 is the implantable antibacterial barrier device of any of Examples 18-27, wherein the housing further includes a wireless power receiver electrically coupled to the barrier circuitry.

Example 29 is an implantable medical device including an elongated medical device and an antibacterial barrier device. The elongated medical device is configured to extend from a subcutaneous pocket, through a vascular entry site and through a portion of a vascular system to a treatment site. The antibacterial barrier device includes a housing configured to be disposed within the subcutaneous pocket, a working electrode configured to be disposed adjacent to the vascular entry site, and a reference electrode configured to be disposed within the subcutaneous pocket. The housing includes barrier circuitry. The working electrode is electrically coupled to the barrier circuitry. The reference electrode is electrically coupled to the barrier circuitry. The barrier circuitry is configured to selectively maintain the working electrode at a negative electrical potential relative to the reference electrode to form an antibacterial barrier.

Example 30 is the implantable medical device of Example 29, wherein the elongated medical device is an electrical lead having a proximal end configured to be coupled to the housing and a distal end configured be disposed adjacent to the treatment site. The implantable medical device further includes stimulation circuitry contained within the housing for providing electro stimulation therapy at the treatment site, and a treatment electrode configured to be electrically coupled to the stimulation circuitry. The treatment electrode is disposed at the distal end.

Example 31 is the implantable medical device of Example 30, wherein the working electrode is integral with the electrical lead.

Example 32 is the implantable medical device of Example 29, wherein the elongated medical device is a catheter having a proximal end configured to be coupled to the housing and a distal end configured to be disposed adjacent to the treatment site, the implantable medical device further comprising a pump contained within the housing for providing chemical therapy to the treatment site.

Example 33 is the implantable medical device of any of Examples 29-32, wherein the working electrode is further configured to be disposed at least partially around the elongated medical device.

Example 34 is the implantable medical device of any of Examples 29-33, wherein the reference electrode includes at least a portion of an exterior surface of the housing.

Example 35 is the implantable medical device of any of Examples 29-34, wherein the reference electrode includes a patch electrode.

Example 36 is the implantable medical device of any of Examples 29-33, wherein the reference electrode is further configured to be disposed at least partially around the elongated medical device.

Example 37 is the implantable antibacterial barrier device of any of Examples 29-36, wherein the housing further includes an energy storage device electrically coupled to the barrier circuitry.

Example 38 is the implantable antibacterial barrier device of any of Examples 29-37, wherein the housing further includes a wireless power receiver electrically coupled to the barrier circuitry.

Example 39 is a method for providing an antibacterial barrier between a subcutaneous pocket and a vascular entry site. The method includes disposing a reference electrode in a subcutaneous pocket, disposing a working electrode in the adjacent to the vascular entry site, and generating an electrical potential at the working electrode that is negative relative to the reference electrode.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
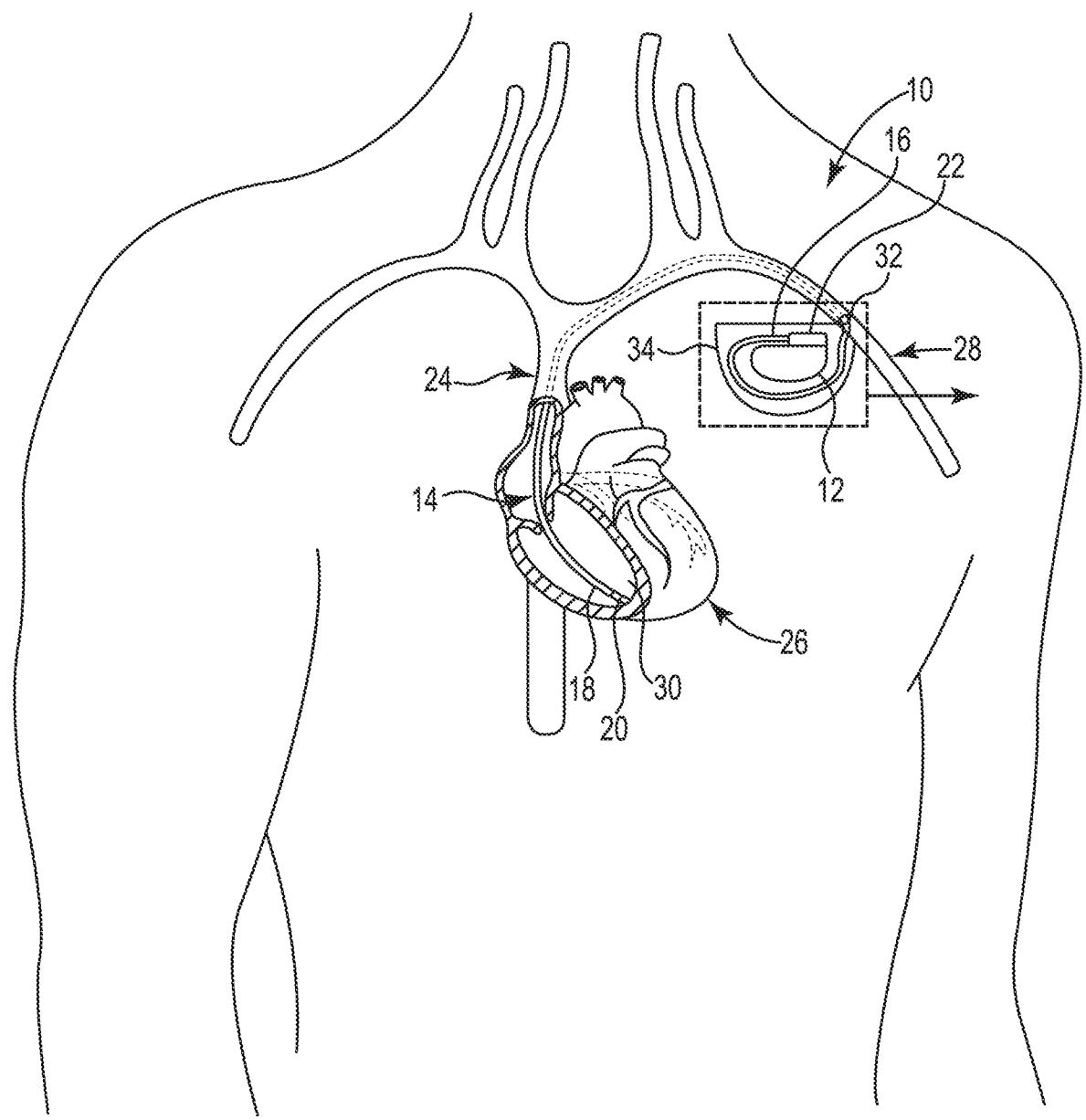
FIG. 1 is a schematic view of an implantable medical device, according to some embodiments of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding is available by reference to the following detailed description of numerous aspects and embodiments of the disclosure. The detailed description which follows is intended to illustrate but not limit the disclosure.

In accordance with various aspects of the disclosure, a medical device is defined as "an implantable medical device" if it is completely or partly introduced, surgically or medically, into the human body, and which is intended to remain after the procedure. It is understood that the various embodiments can be implemented in any suitable medical device implanted in a patient that includes an elongated medical device, such as, without limitation, cardiac rhythm management (CRM) systems (e.g., a cardioverter-defibrillator (ICD) system, a pacemaker system, or a cardiac resynchronization system), implantable cardiac monitors, neurostimulation systems (e.g., a spinal cord stimulation system, a deep brain stimulation system, an overactive bladder system, a hypoglossal nerve stimulation system, or a vagus nerve stimulation system), implantable incontinence systems, implantable erectile dysfunction systems, implantable drug delivery systems, intravenous catheters, temporary ventricular support devices, intra-aortic balloon pumps, dialysis shunts, urinary catheters, and endotracheal tubes.

FIG. 1 provides an illustrative but non-limiting example of a medical application using an implantable medical device suitable for use with an antibacterial barrier device implanted into a subcutaneous pocket to prevent a bacterial infection from spreading from the subcutaneous pocket into the circulatory system, including the vasculature and the heart. As is known in the art, cell walls of bacteria hold a negative charge. Embodiments of the present disclosure make use of this characteristic of bacteria to form an antibacterial barrier by generating an electrical field that causes the bacteria in the subcutaneous pocket, which might otherwise migrate into the circulatory system, to remain within the subcutaneous pocket. The application and location are illustrative only, as implantable medical devices according to embodiments of the present disclosure may be used in a variety of anatomical locations.

FIG. 1 is a schematic view of an implantable medical device suitable for use with an antibacterial barrier device, in accordance with embodiments of the disclosure. FIG. 1 illustrates an exemplary implantable medical device (IMD) 10 in the form of a cardiac rhythm management system. As shown in FIG. 1, the IMD 10 may include housing 12 and an elongated medical device in the form of an electrical lead 14. Although a single electrical lead 14 is shown, it is understood that the disclosure includes embodiment including multiple electrical leads 14. The electrical lead 14 includes a proximal end 16, a distal end 18, and a treatment electrode 20 disposed at the distal end 18. The proximal end 16 is configured to be coupled to the housing 12 by, for example, plugging into a header 22 of the housing 12. The electrical lead 14 also includes conductors (not shown) as necessary to convey electrical pulses and signals between the housing 12 and the treatment electrode 20.

As shown in FIG. 1, a patient's circulatory system 24 includes a heart 26 and vasculature 28. The electrical lead 14 can enter the vasculature 28 through a vascular entry site 32 formed in a wall of the vasculature 28. The distal end 18 of the electrical lead 14 is configured to be disposed adjacent to a treatment site 30 within the heart 26. The housing 12 can be implanted in a subcutaneous pocket 34 formed in a patient's chest, as shown in FIG. 1, for example. A portion of the electrical lead 14 extending from the housing 12 to the vascular entry site 32 is also be located within the subcutaneous pocket 34.

Figure 2:
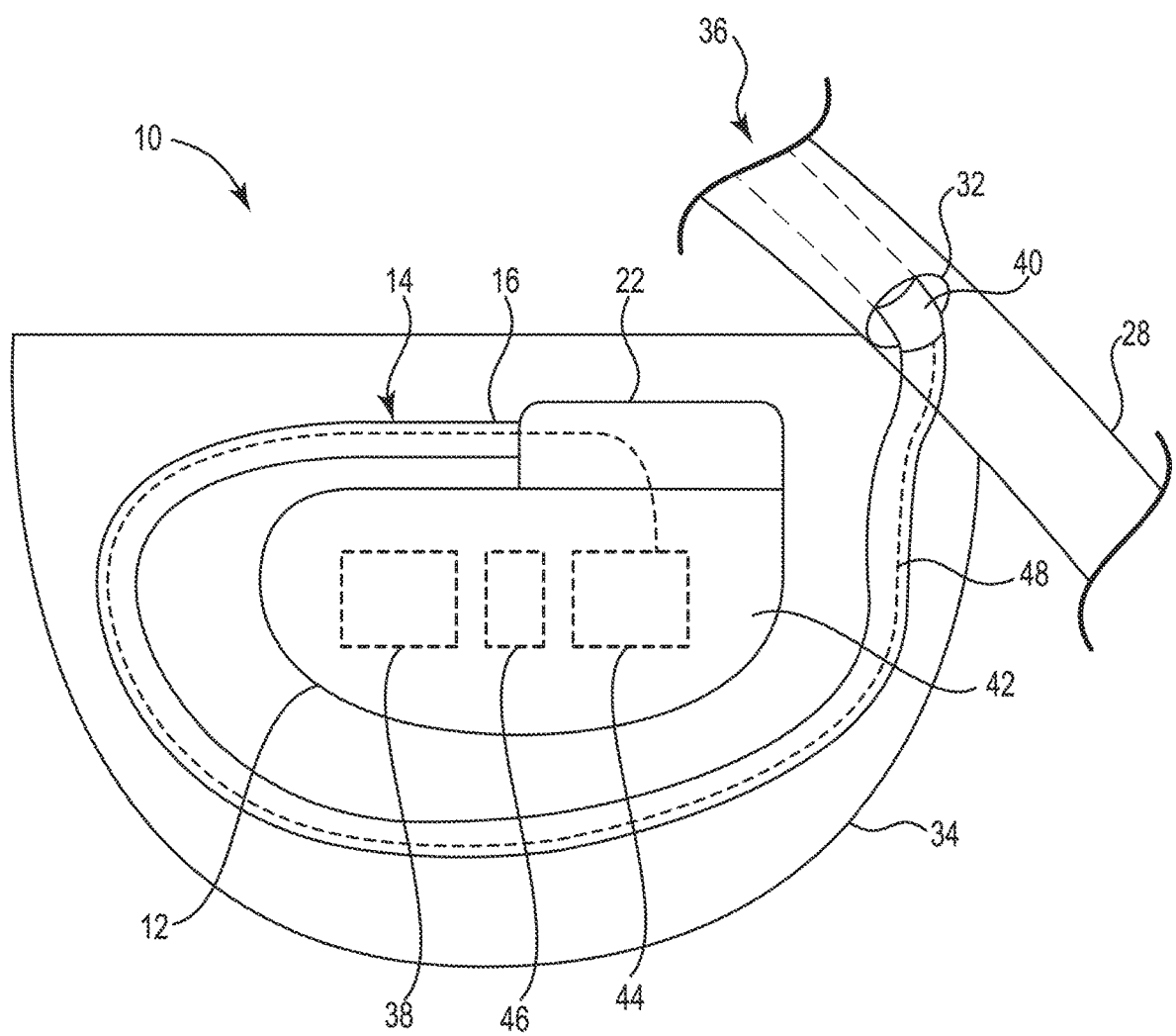
FIG. 2 is an enlarged schematic view of a portion of the implantable medical device of FIG. 1 including an antibacterial barrier device subcutaneously implanted within a patient, according to some embodiments of the disclosure.

FIG. 2 is an enlarged schematic view of a portion of the implantable medical device 10 of FIG. 1 including an antibacterial barrier device 36 subcutaneously implanted within a patient, according to some embodiments of the disclosure. In the embodiment of FIG. 2, the housing 12 includes stimulation circuitry 38 for providing electro stimulation therapy at the treatment site 30 by way of a conductor (not shown) extending through the electrical lead 14 from the proximal end 16 to the treatment electrode 20 at the distal end 18 (FIG. 1). The antibacterial barrier device 36 includes the housing 12, a working electrode 40 and a reference electrode 42. The antibacterial barrier device 36 further includes barrier circuitry 44 and an energy storage device 46 disposed within the housing 12.

The working electrode 40 is an electrically conductive ring or cylinder that extend entirely or substantially around the electrical lead 14. The working electrode 40 is integral with the electrical lead 14. That is, the working electrode 40 is incorporated into the electrical lead 14 when the electrical lead 14 is produced and it cannot be removed from the electrical lead 14 without compromising the integrity of the electrical lead 14. The working electrode 40 may be formed of any biocompatible electrical conductor, such as titanium or stainless steel, for example. The working electrode 40 is configured to be disposed adjacent to the vascular entry site 32 by being formed along the electrical lead 14 such that when the distal end 18 is disposed at the treatment site 30, the working electrode 40 is adjacent to the vascular entry site 32. As used herein, adjacent to the vascular entry site 32 means disposed within the vascular entry site 32, as shown in FIG. 2, or within about 5 cm of the vascular entry site 32.

The working electrode 40 is electrically coupled to the barrier circuitry 44 by a conductor 48 extending through the electrical lead 14 from the working electrode 40 to the barrier circuitry 44 within the housing 12. The conductor 48 may be a series of multiple conductors, such as a wire extending from the working electrode 40 to the proximal end 16 of the electrical lead 14, a spring contact within the header 22, and another wire extending from the header 22 to the barrier circuitry 44, for example.

In the embodiment of FIG. 2, at least a portion of the exterior surface of the housing 12 serves as the reference electrode 42. Thus, the reference electrode 42 is configured to be disposed within the subcutaneous pocket 34 when the housing 12 is implanted. The housing 12 can be formed, at least in part, of a biocompatible electrical conductor, such as titanium or stainless steel, for example. The housing 12, and thus the reference electrode 42, is electrically coupled to the barrier circuitry 44. The barrier circuitry 44 is configured, as described below in FIG. 6, to selectively maintain the working electrode 40 at a negative electrical potential relative to the reference electrode 42.

The energy storage device 46 may be a chemical battery, a storage capacitor, or any other type of energy storage device capable of producing an electrical potential. The energy storage device 46 is electrically coupled to the barrier circuitry 44. The energy storage device 46 may also be electrically coupled to the stimulation circuitry 38.

Once the implanted in a patient by disposing the working electrode 40 adjacent to the vascular entry site 32 and disposing the housing 12 (and reference electrode 42) in the subcutaneous pocket 34 as shown in FIG. 2, the barrier circuitry 44 can generate an electrical potential at the working electrode 40 that is negative relative to the reference electrode 42. This electrical potential difference forms an antibacterial barrier by generating an electrical field that causes bacteria in the subcutaneous pocket 34, which might otherwise migrate through the vascular entry site 32, to migrate away from the vascular entry site 32. The negatively charged bacteria migrate away from the negative working electrode 40 adjacent to the vascular entry site 32 and toward the more positive reference electrode 42 in the subcutaneous pocket 34.

The electrical potential at the working electrode 40 that is negative relative to the reference electrode 42 can be generated in a way that reduces, or eliminates, interactions with any therapy delivery or measurements conducted by the electrical lead 14. For example, generation of the electrical potential and the therapy delivery or measurements can be coordinated to not occur simultaneously. Alternatively, any measurements made during the generation of the electrical potential can be discarded.

Figure 3:
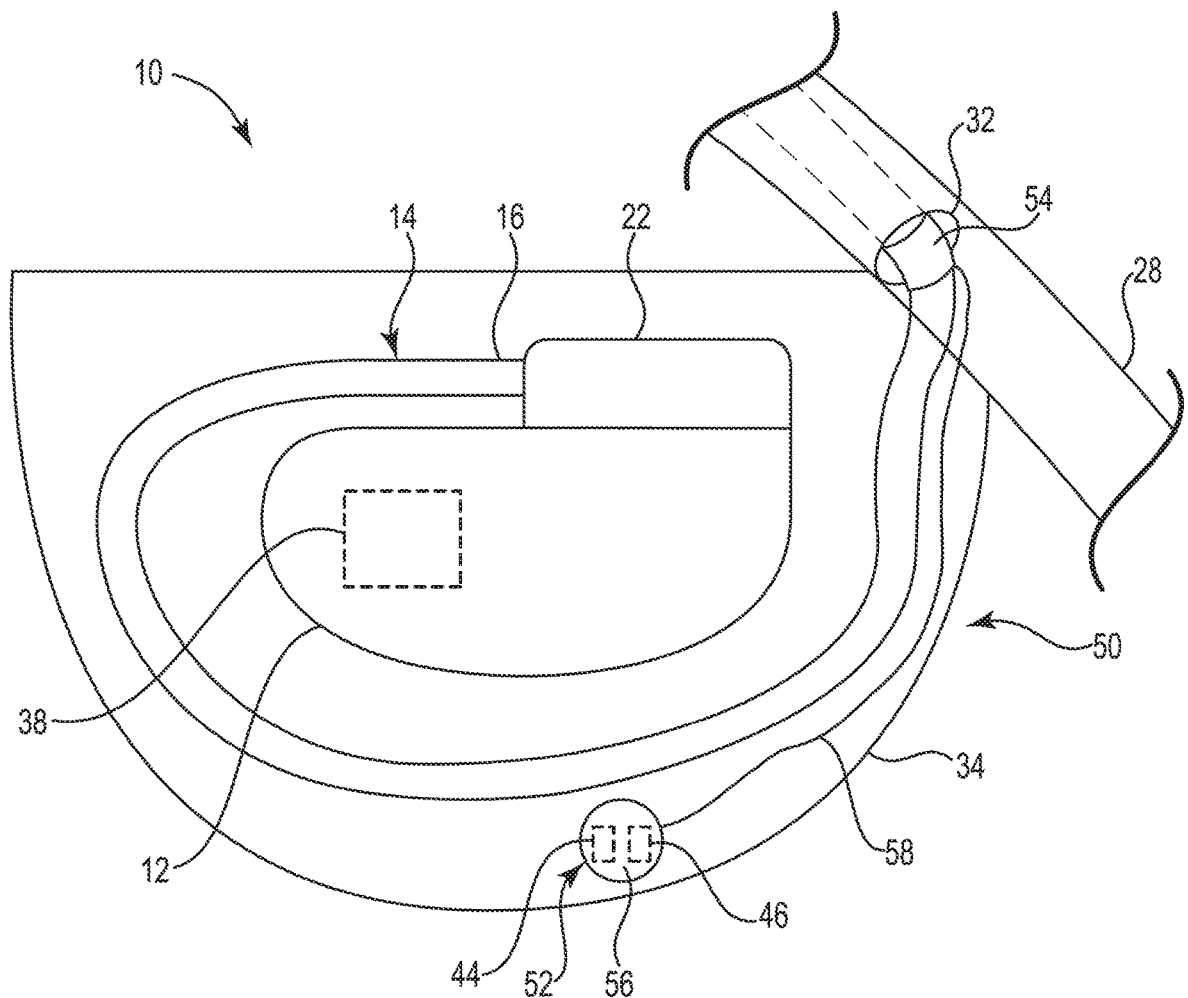
FIG. 3 is an enlarged schematic view of a portion of the implantable medical device of FIG. 1 including an antibacterial barrier device subcutaneously implanted within a patient, according to some other embodiments of the disclosure.

FIG. 3 is an enlarged schematic view of a portion of the implantable medical device 10 of FIG. 1 including an antibacterial barrier device 50 subcutaneously implanted within a patient, according to some other embodiments of the disclosure. As with the embodiment of FIG. 2, the housing 12 includes stimulation circuitry 38 for providing electro stimulation therapy at the treatment site 30 by way of a conductor (not shown) extending through the electrical lead 14 from the proximal end 16 to the treatment electrode 20 at the distal end 18 (FIG. 1). However, in contrast to the embodiment of FIG. 2, the housing 12 is not part of, and does not include, any components of the antibacterial barrier device 50. The antibacterial barrier device 50 includes a housing 52 (separate from the housing 12), a working electrode 54 and a reference electrode 56. The antibacterial barrier device 50 further includes the barrier circuitry 44 and the energy storage device 46, as described above in reference to FIG. 2, disposed within the housing 52.

In the embodiment of FIG. 3, the working electrode 54 is an electrically conductive cylinder or cuff that extends entirely or substantially around the electrical lead 14. The working electrode 54 is not integral with the electrical lead 14. That is, the working electrode 54 may be slid over, wrapped around and/or fastened onto the electrical lead 14 after the electrical lead 14 is produced, such as at the time of implantation, and it can be removed from the electrical lead 14 without compromising the integrity of the electrical lead 14. The working electrode 54 may be formed of any biocompatible electrical conductor, such as titanium or stainless steel, for example. The working electrode 54 is configured to be disposed adjacent to the vascular entry site 32 by being moved or placed along the electrical lead 14 such that when the distal end 18 is disposed at the treatment site 30, the working electrode 54 is adjacent to the vascular entry site 32.

The working electrode 54 is electrically coupled to the barrier circuitry 44 by a conductor 58 extending through the subcutaneous pocket 34 from the working electrode 54 to the barrier circuitry 44 within the housing 52. Although the conductor 58 is shown as a single conductor, it is understood that the conductor 58 may be a series of multiple conductors.

Figure 6:
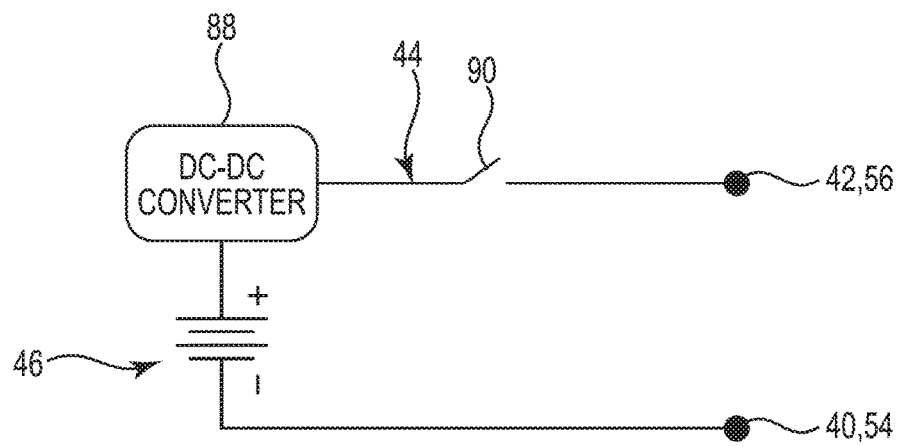
FIG. 6 is schematic diagram of a barrier circuit and energy storage device for the antibacterial barrier device, according to some embodiments of the disclosure.

In the embodiment of FIG. 3, at least a portion of the exterior surface of the housing 52 serves as the reference electrode 56. Thus, the reference electrode 56 is configured to be disposed within the subcutaneous pocket 34 when the housing 52 is implanted. The housing 52 can be formed, at least in part, of a biocompatible electrical conductor, such as titanium or stainless steel, for example. The reference electrode 56, is electrically coupled to the barrier circuitry 44. The barrier circuitry 44 is configured, as shown in FIG. 6, to selectively maintain the working electrode 54 at a negative electrical potential relative to the reference electrode 56.

As with the embodiment of FIG. 2, the energy storage device 46 is electrically coupled to the barrier circuitry 44. However, in contrast to the embodiment of FIG. 2, the energy storage device 46 is not electrically coupled to the stimulation circuitry 38, which can be powered by other means, such as another energy storage device (not shown), for example.

Once the electrical lead 14 is implanted in a patient, the working electrode 54 can be attached to, wrapped around, or slid onto the electrical lead 14, and moved or placed along the electrical lead 14 so that it is adjacent to the vascular entry site 32. The housing 52 (and reference electrode 56) can be disposed in the subcutaneous pocket 34 as shown in FIG. 3. The barrier circuitry 44 can generate an electrical potential at the working electrode 54 that is negative relative to the reference electrode 56. This electrical potential difference forms an antibacterial barrier by generating an electrical field that causes bacteria in the subcutaneous pocket 34, which might otherwise migrate through the vascular entry site 32, to migrate away from the vascular entry site 32. The negatively charged bacteria migrate away from the negative working electrode 54 adjacent to the vascular entry site 32 and toward the more positive reference electrode 56 in the subcutaneous pocket 34.

Figure 4:
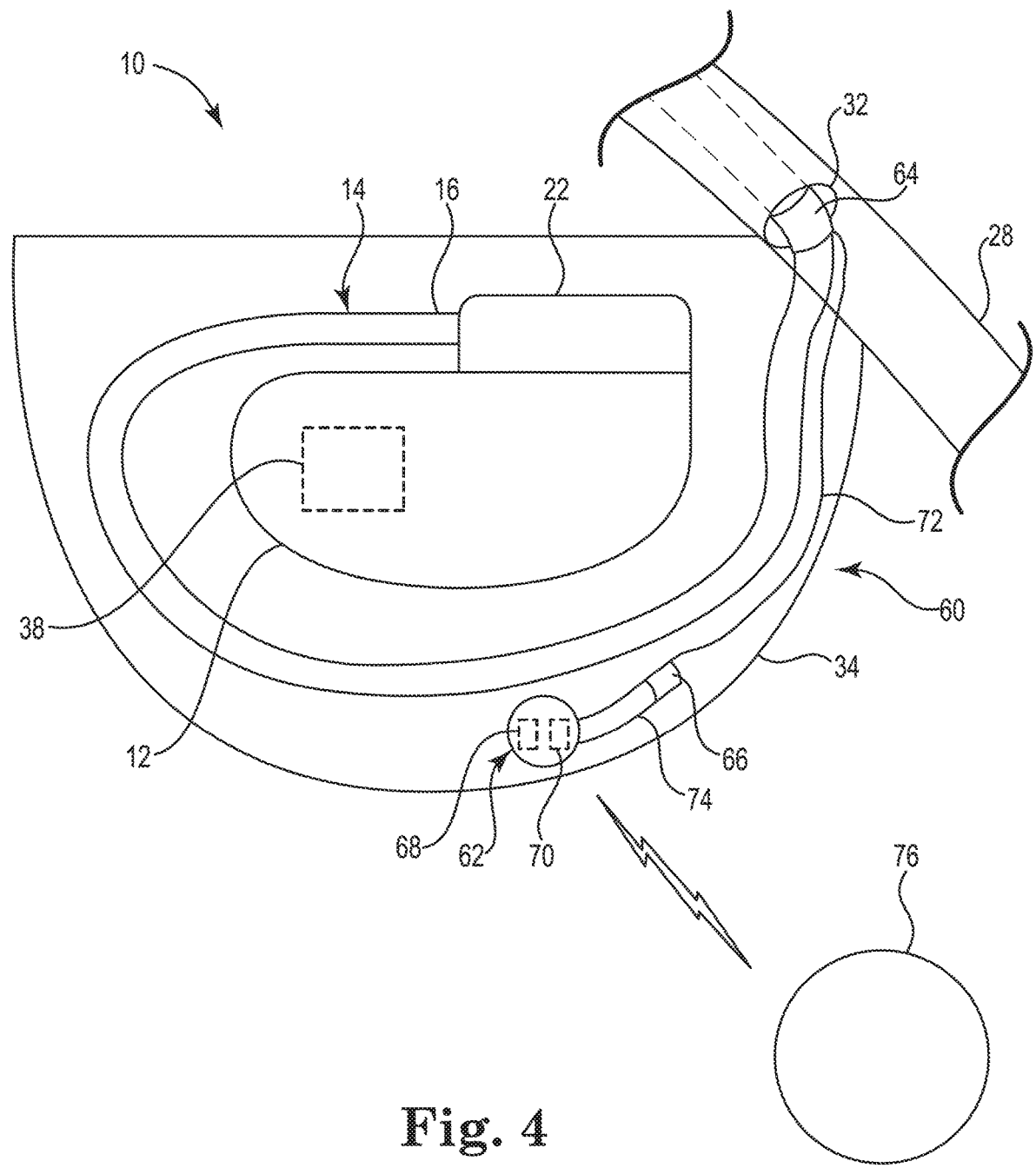
FIG. 4 is an enlarged schematic view of a portion of the implantable medical device of FIG. 1 including an antibacterial barrier device subcutaneously implanted within a patient, according to some other embodiments of the disclosure.

FIG. 4 is an enlarged schematic view of a portion of the implantable medical device 10 of FIG. 1 including an antibacterial barrier device 60 subcutaneously implanted within a patient, according to some other embodiments of the disclosure. As with the embodiment of FIG. 2, the housing 12 includes stimulation circuitry 38 for providing electro stimulation therapy at the treatment site 30 by way of a conductor (not shown) extending through the electrical lead 14 from the proximal end 16 to the treatment electrode 20 at the distal end 18 (FIG. 1). However, in contrast to the embodiment of FIG. 2, the housing 12 is not part of, and does not include, any components of the antibacterial barrier device 60. The antibacterial barrier device 60 includes a housing 62 (separate from the housing 12), a working electrode 64 and a reference electrode 66. The antibacterial barrier device 60 further includes barrier circuitry 68 and a wireless power receiver 70 disposed within the housing 62.

In the embodiment of FIG. 4, the working electrode 64 is substantially similar to the working electrode 54 described above in reference to FIG. 3. As with the working electrode 54 of FIG. 3, the working electrode 64 is configured to be disposed adjacent to the vascular entry site 32 by being moved or placed along the electrical lead 14 such that when the distal end 18 is disposed at the treatment site 30, the working electrode 64 is adjacent to the vascular entry site 32. The working electrode 64 is electrically coupled to the barrier circuitry 68 by a conductor 72 extending through the subcutaneous pocket 34 from the working electrode 64 to the barrier circuitry 68 within the housing 62. Although the conductor 72 is shown as a single conductor, it is understood that the conductor 72 may be a series of multiple conductors.

The reference electrode 66 is a patch electrode which can be physically attached to the conductor 72 to position the reference electrode 66 within the subcutaneous pocket 34. The reference electrode 66 is electrically isolated from the conductor 72. The reference electrode 66 is electrically coupled to the barrier circuitry 68 by a second conductor 74 extending through the subcutaneous pocket 34 from the reference electrode 66 to the barrier circuitry 68 within the housing 62. The reference electrode 66 can be formed, at least in part, of a biocompatible electrical conductor, such as titanium or stainless steel, for example. The barrier circuitry 68 is configured, as described below in FIG. 7, to selectively maintain the working electrode 64 at a negative electrical potential relative to the reference electrode 66.

The wireless power receiver 70 is electrically coupled to the barrier circuitry 68. The wireless power receiver 70 can be inductively or capacitively coupled to a wireless power transmitter 76 which is disposed outside the patient, as described below in reference to FIG. 7. The wireless power receiver 70 is not electrically coupled to the stimulation circuitry 38, which can be powered by other means, such as another energy storage device (not shown), for example.

Once the electrical lead 14 is implanted in a patient, the working electrode 64 can be attached to, wrapped around, or slid onto the electrical lead 14, and moved or placed along the electrical lead 14 so that it is adjacent to the vascular entry site 32. The housing 62 and reference electrode 66 can be disposed in the subcutaneous pocket 34 as shown in FIG. 4. The barrier circuitry 68 can generate an electrical potential at the working electrode 64 that is negative relative to the reference electrode 66. This electrical potential difference forms an antibacterial barrier by generating an electrical field that causes bacteria in the subcutaneous pocket 34, which might otherwise migrate through the vascular entry site 32, to migrate away from the vascular entry site 32. The negatively charged bacteria migrate away from the negative working electrode 64 adjacent to the vascular entry site 32 and toward the more positive reference electrode 66 in the subcutaneous pocket 34.

Figure 5:
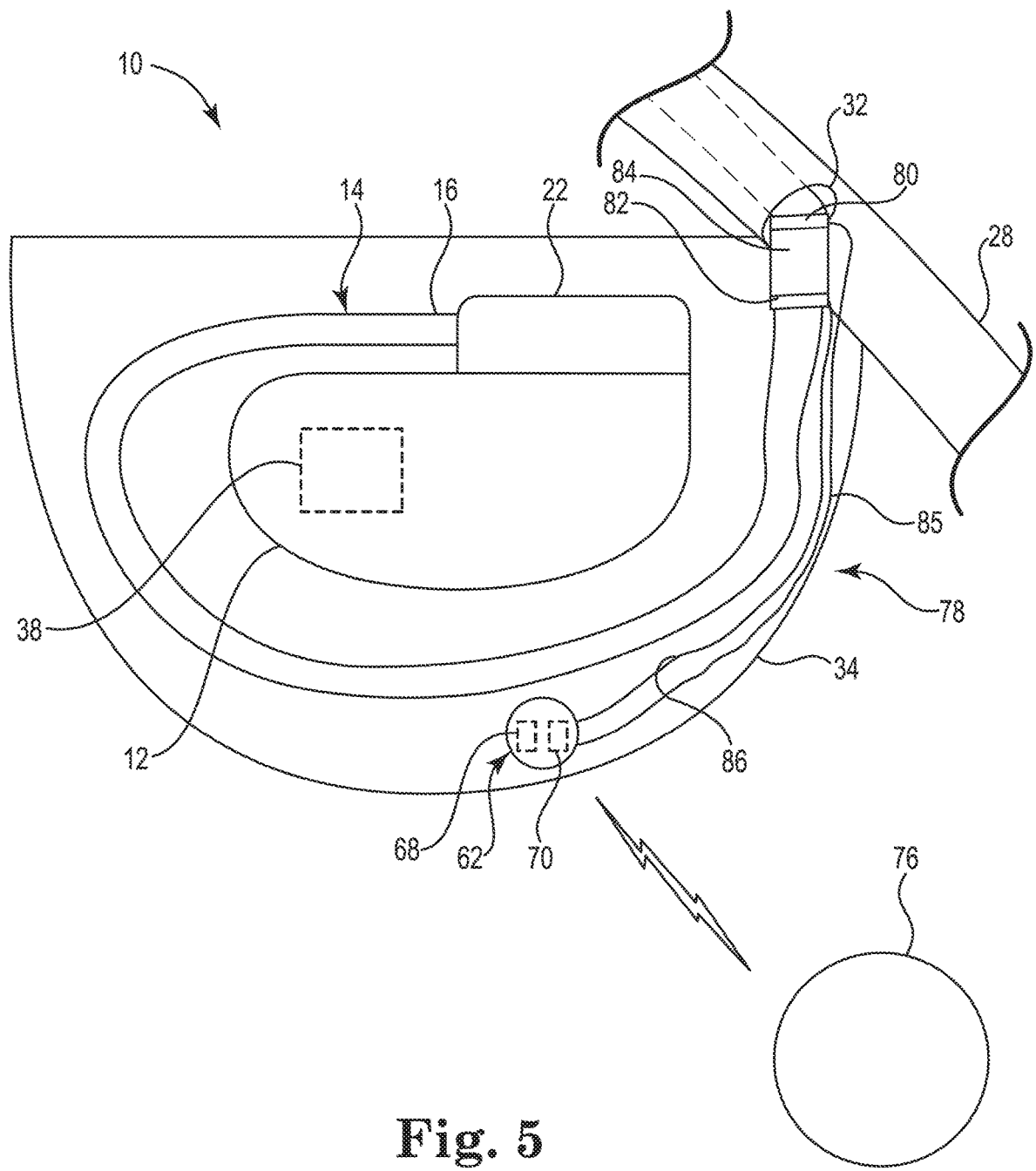
FIG. 5 is an enlarged schematic view of a portion of the implantable medical device of FIG. 1 including an antibacterial barrier device subcutaneously implanted within a patient, according to some other embodiments of the disclosure.

FIG. 5 is an enlarged schematic view of a portion of the implantable medical device 10 of FIG. 1 including an antibacterial barrier device 78 subcutaneously implanted within a patient, according to some other embodiments of the disclosure. As with the embodiment of FIG. 2, the housing 12 includes stimulation circuitry 38 for providing electro stimulation therapy at the treatment site 30 by way of a conductor (not shown) extending through the electrical lead 14 from the proximal end 16 to the treatment electrode 20 at the distal end 18 (FIG. 1). However, in contrast to the embodiment of FIG. 2, the housing 12 is not part of, and does not include, any components of the antibacterial barrier device 78. The antibacterial barrier device 78 includes the housing 62, a working electrode 80, a reference electrode 82, and a spacer 84. The antibacterial barrier device 78 further includes barrier circuitry 68 and a wireless power receiver 70 disposed within the housing 62 as described above in reference to FIG. 4.

In the embodiment of FIG. 5, the working electrode 80 and the reference electrode 82 are electrically conductive cylinders or cuffs that extend entirely or substantially around the electrical lead 14. The working electrode 80 and the reference electrode 82 are not integral with the electrical lead 14. The working electrode 80 and the reference electrode 82 may be formed of any biocompatible electrical conductor, such as titanium or stainless steel, for example. The spacer 84 is an electrically insulative cylinder or cuff that extends entirely or substantially around the electrical lead 14. The spacer may be formed of any biocompatible electrical insulator, such as a polymer (e.g., polyurethane or silicone rubber), for example.

The working electrode 80 and the reference electrode 82 are coupled to the spacer 84 and spaced apart from each other. In some embodiments, the working electrode 80 and the reference electrode 82 are coupled to opposite ends of the spacer 84, as shown in FIG. 5. The working electrode 80 is configured to be disposed adjacent to the vascular entry site 32 by moving or placing the working electrode 80 along the electrical lead 14 such that when the distal end 18 is disposed at the treatment site 30, the working electrode 80 is adjacent to the vascular entry site 32 and the reference electrode is disposed in the subcutaneous pocket 34, as shown in FIG. 5.

The working electrode 80 is electrically coupled to the barrier circuitry 68 by a conductor 85 extending through the subcutaneous pocket 34 from the working electrode 80 to the barrier circuitry 68 within the housing 62. The reference electrode 82 is also electrically coupled to the barrier circuitry 68 by a second conductor 86 extending through the subcutaneous pocket 34 from the reference electrode 82 to the barrier circuitry 68 within the housing 62. The barrier circuitry 68 is configured, as described below in FIG. 7, to selectively maintain the working electrode 80 at a negative electrical potential relative to the reference electrode 82. The wireless power receiver 70 is electrically coupled to the barrier circuitry 68 and is as described above in reference to FIG. 4.

Once the electrical lead 14 is implanted in a patient, the spacer 84 with the working electrode 80 and the reference electrode 82 can be coupled to, wrapped around, or slid onto the electrical lead 14, and placed or moved along the electrical lead 14 so that the working electrode 80 is adjacent to the vascular entry site 32 and the reference electrode 82 is disposed with in the subcutaneous pocket. The barrier circuitry 68 can generate an electrical potential at the working electrode 80 that is negative relative to the reference electrode 82 to form an antibacterial barrier as described above.

In the embodiments describe above, the reference electrode 42, 56, 66, 82 is spaced apart from the working electrode 40, 54, 64, 80 by a distance as small as 1 cm, 2 cm, 3 cm, 4 cm, or 5 cm or as large as 6 cm, 7 cm, 8 cm, 9 cm, or 10, cm or by a distance within any range defined between any two of the foregoing values, such as from 1 cm to 10 cm, 2 cm to 9 cm, 3 cm to 8 cm, 4 cm to 7 cm, 5 cm to 6 cm, 2 cm to 3 cm, or 2 cm to 5 cm, for example. Larger spacings between the electrodes increases the resistance between them, reducing the drain on the battery. Smaller spacings increase the strength of the electrical field, enhancing the movement of bacteria away from the working electrode 40, 54, 64, 80.

In some embodiments, the reference electrode 42, 56, 66, 82 may include an antibiotic coating such that bacteria drawn away from working electrode 40, 54, 64, 80 and to the reference electrode 42, 56, 66, 82 may be killed upon reaching the reference electrode 42, 56, 66, 82.

FIG. 6 is schematic diagram of barrier circuit and an energy storage device for the antibacterial barrier device, according to some embodiments of the disclosure. FIG. 6 shows that the barrier circuit 44 and the energy storage device 46 electrically connected to the barrier circuit 44. The barrier circuit 44 includes a DC-DC converter 88 and a switch 90. The DC-DC converter 88 converts the voltage of the energy storage device 46 to produce a desired electrical potential between the working electrode 40, 54 and the reference electrode 42, 56. The energy storage device 46 may produce a voltage between 1.5 V and 3.5 V, for example. The desired electrical potential between the working electrode 40, 54 and the reference electrode 42, 56 may be between 10 mV and 1 V.

The switch 90 selectively activates the antibacterial barrier 36, 50. The switch 90 may be activated continuously until depletion of the energy storage device 46 or until deactivated by a caregiver. Alternatively, the switch 90 may be selectively activated so that the antibacterial barrier 36, 50 is activated for a period of time following implantation, when the danger from an infection is at its greatest, and then deactivated once the danger is passed. In this way, the lifetime of the energy storage device 46 may be preserved for embodiments in which the energy storage device 46 also powers the electro stimulation therapy (FIG. 2). The switch 90 may be cyclically activated so that the duration of each activation is between 0.1 mS and 1.0 mS to prevent undesirable tissue interaction, such as muscle stimulation or pain, for example.

Figure 7:
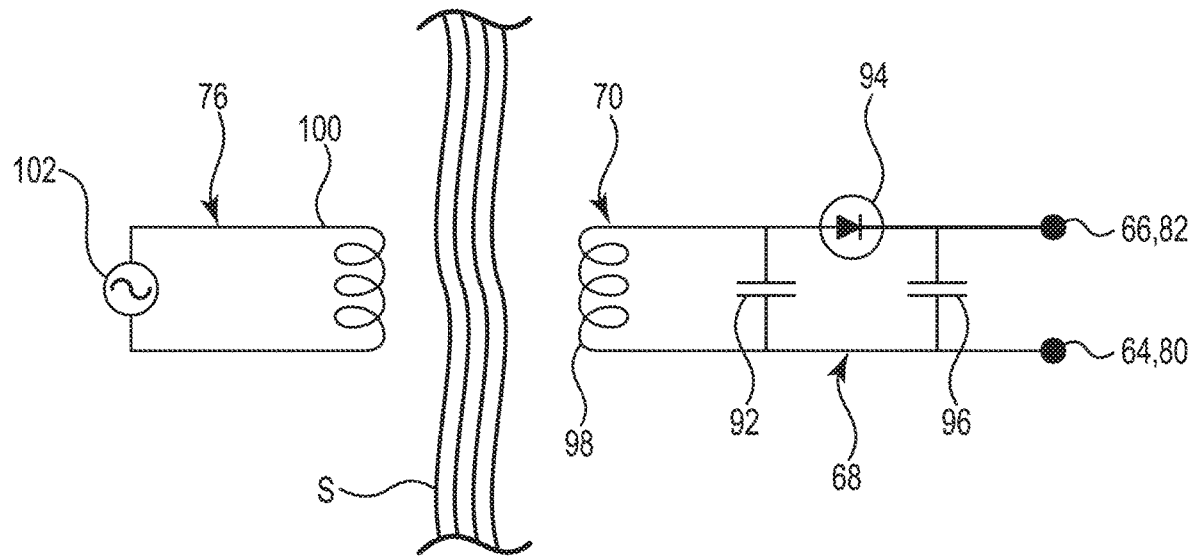
FIG. 7 is schematic diagram of a barrier circuit and wireless power receiver for the antibacterial barrier device, according to some other embodiments of the disclosure.

FIG. 7 is schematic diagram of a barrier circuit and a wireless power device for the antibacterial barrier device, according to some other embodiments of the disclosure. FIG. 7 shows that the barrier circuit 68 includes a resonating capacitor 92, a diode 94 and a supply capacitor 96. The wireless power receiver 70 includes a receiving coil 98. The wireless power transmitter 76 includes a transmitting coil 100 and an alternating current (AC) power supply 102 electrically connected to the transmitting coil 100. As the wireless power transmitter 76 is outside of the patient, the patient's skin S separates the transmitting coil 100 from the receiving coil 98.

In use, the transmitting coil 100 generates an alternating magnetic field from an alternating voltage from the AC power supply 102. The alternating magnetic field transmits through the skin S and induces an alternating voltage across the receiving coil 98. The diode 94 converts the induced AC voltage to a DC voltage. The resonating capacitor establishes the center frequency. The supply capacitor 96 filters the DC voltage to produce a desired electrical potential between the working electrode 64, 80 and the reference electrode 66, 82.

Although the antibacterial barrier devices 36 and 50 are shown employing the energy storage device 46 and the antibacterial barrier devices 60 and 78 are shown employing the wireless power receiver 70, it is understood that any of the antibacterial devices described above may employ either or both of the energy storage device 46 and the wireless power receiver 70.

Although the implantable antibacterial devices 36, 50, 60 and 78 are shown and described in which the elongated medical device is an electrical lead, it is understood that embodiment include those in which the elongated medical device is a catheter having a proximal end 16 configured to be coupled to the housing 12 and a distal end 18 configured be disposed adjacent to the treatment site 30. The implantable medical device can further comprise a pump contained within the housing 12 for providing chemical therapy to the treatment site 30, for example.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An implantable antibacterial barrier device for an elongated medical device, the elongated medical device configured to extend from a first site, through a second site, to a third site, the implantable antibacterial barrier device comprising:
    a housing configured to be disposed at the first site, the housing comprising barrier circuitry;
    a working electrode configured to be disposed at the second site, the working electrode electrically coupled to the barrier circuitry; and
    a reference electrode configured to be disposed at the first site and spaced apart from the working electrode, the reference electrode electrically coupled to the barrier circuitry, the barrier circuitry configured to selectively maintain the working electrode at a negative electrical potential relative to the reference electrode to form an antibacterial barrier.

2. The implantable antibacterial barrier device of claim 1, wherein the first site is a subcutaneous pocket.

3. The implantable antibacterial barrier device of claim 1, wherein the second site is adjacent to a vascular entry site and the elongated medical device is configured to extend through the vascular entry site and through a portion of a vascular system to the third site.

4. The implantable antibacterial barrier device of claim 1, wherein the third site is at least one selected from the group consisting of a treatment site and a measurement site.

5. The implantable antibacterial barrier device of claim 1, wherein the reference electrode is configured to be spaced apart from the working electrode by at least 1 cm.

6. The implantable antibacterial barrier device of claim 1, wherein the working electrode is further configured to be disposed at least partially around the elongated medical device.

7. The implantable antibacterial barrier device of claim 1, wherein the reference electrode includes at least a portion of an exterior surface of the housing.

8. The implantable antibacterial barrier device of claim 1, wherein the reference electrode includes a patch electrode.

9. The implantable antibacterial barrier device of claim 1, wherein the reference electrode is further configured to be disposed at least partially around the elongated medical device.

10. The implantable antibacterial barrier device of claim 1, wherein the housing further includes an energy storage device electrically coupled to the barrier circuitry.

11. The implantable antibacterial barrier device of claim 1, wherein the housing further includes a wireless power receiver electrically coupled to the barrier circuitry.

12. An implantable medical device comprising:
    an elongated medical device, the elongated medical device configured to extend from a subcutaneous pocket, through a vascular entry site and through a portion of a vascular system to a treatment site; and
    an antibacterial barrier device comprising:
        a housing configured to be disposed within the subcutaneous pocket, the housing comprising barrier circuitry;
        a working electrode configured to be disposed adjacent to the vascular entry site, the working electrode electrically coupled to the barrier circuitry; and
        a reference electrode configured to be disposed within the subcutaneous pocket, the reference electrode electrically coupled to the barrier circuitry, the barrier circuitry configured to selectively maintain the working electrode at a negative electrical potential relative to the reference electrode to form an antibacterial barrier.

13. The implantable medical device of claim 12, wherein the elongated medical device is an electrical lead having a proximal end configured to be coupled to the housing and a distal end configured be disposed adjacent to the treatment site, the implantable medical device further comprising:
    stimulation circuitry contained within the housing for providing electro stimulation therapy at the treatment site; and
    a treatment electrode configured to be electrically coupled to the stimulation circuitry, the treatment electrode disposed at the distal end.

14. The implantable medical device of claim 13, wherein the working electrode is integral with the electrical lead.

15. The implantable medical device of claim 12, wherein the working electrode is further configured to be disposed at least partially around the elongated medical device.

16. The implantable medical device of claim 12, wherein the reference electrode includes at least a portion of an exterior surface of the housing.

17. The implantable medical device of claim 12, wherein the reference electrode includes a patch electrode.

18. The implantable medical device of claim 12, wherein the reference electrode is further configured to be disposed at least partially around the elongated medical device.

19. The implantable medical device of claim 12, wherein the housing further includes an energy storage device electrically coupled to the barrier circuitry.

20. A method for providing an antibacterial barrier between a subcutaneous pocket and a vascular entry site, the method comprising:
    disposing a reference electrode in the subcutaneous pocket;
    disposing a working electrode adjacent to the vascular entry site; and
    generating an electrical potential at the working electrode that is negative relative to the reference electrode.

* * * * *